US009433522B2

(12) United States Patent
Bader

(10) Patent No.: US 9,433,522 B2
(45) Date of Patent: Sep. 6, 2016

(54) ANKLE-FOOT ORTHOSIS

(71) Applicant: Wade Bader, Lutz, FL (US)

(72) Inventor: Wade Bader, Lutz, FL (US)

(*) Notice: Subject to any disclaimer, the term of this patent is extended or adjusted under 35 U.S.C. 154(b) by 137 days.

(21) Appl. No.: 13/987,740

(22) Filed: Aug. 27, 2013

(65) Prior Publication Data

US 2015/0065934 A1    Mar. 5, 2015

(51) Int. Cl.
*A61F 5/00* (2006.01)
*A61F 5/01* (2006.01)

(52) U.S. Cl.
CPC ............ *A61F 5/0127* (2013.01); *A61F 5/0111* (2013.01)

(58) Field of Classification Search
CPC .................. A61F 2002/5018; A61F 2002/701; A61F 2002/704; A61F 2002/705; A61F 2002/7635; A61F 2002/764; A61F 2/6607; A61F 2/68; A61F 2/72; A61F 2002/7645; A61F 2002/5073; A61F 2002/7625; A61F 5/0127; A61F 2005/0179; A61F 5/14; A61F 2005/0139; A61F 2005/0169; A61F 5/0123; A61F 5/0125; A61F 5/0102; A61F 2/66; A61F 5/102; A61F 2002/30434; A61F 2002/30438; A61F 2002/5053; A61F 2002/6678; A61F 2002/6685; A43B 13/143; A43B 17/00; A43B 13/14; A43B 13/181; A43B 13/20; A61K 45/06; A61L 2300/404; A61L 2300/416; A61L 2300/432; A61L 27/54; A61L 31/16
USPC ........................... 602/23–28; 128/882; 5/624
See application file for complete search history.

(56) References Cited

U.S. PATENT DOCUMENTS 5,775,008 A * 7/1998 Bussell et al. .................... 36/89
7,524,295 B1 * 4/2009 Peters et al. ....................... 602/5
2007/0027421 A1 * 2/2007 Nobbe et al. .................... 602/27

* cited by examiner

*Primary Examiner* — Michael Brown
(74) *Attorney, Agent, or Firm* — Arthur W. Fisher, III

(57) ABSTRACT

An ankle-foot orthosis constructed of composite material to assist a person with a foot infirmity in walking comprising an upper arcuate convex shell to engage the anterior of the lower leg and a lower foot support member to engage and support the foot coupled together by an inverted substantially wishbone or Y-shaped intermediate interconnecting member including an upper elongated substantially vertical interconnecting member integrally formed with the upper arcuate convex shell and a lower arcuate convex lateral interconnecting member extending from the lower end portion of the upper elongated substantially vertical interconnecting member to each side of the lower foot support member.

18 Claims, 10 Drawing Sheets

ANKLE-FOOT ORTHOSIS

BACKGROUND

1. Field of the Invention

An ankle-foot orthosis to assist a person with foot infirmity in walking.

2. Description of the Prior Art

There are numerous orthotic devices designed to assist infirmed individuals to ambulate shown in the prior art.

For example, De La Torre Orthotics and Prosthetics has developed a two-piece articulated ankle foot orthosis, floor reaction device to provide ground reaction forces to the knee which assist in stabilizing the knee during ambulation that can be seen at http://www.delatorreop.com Several other examples are described below.

U.S. Pat. No. 5,044,360 relates to a releasable controlled-motion ankle-foot orthosis comprising an elongated shell adapted for releasable attachment to the lower leg above the ankle joint, a foot support adapted for releasable attachment to the foot, and lateral and medial controlled-motion ankle joint assemblies attached to the shell and to the foot support in alignment with the axis of rotation through the ankle joint. Each cam member is rotatably mounted to the support plate for contact with a stop on the support plate to control angular motion.

U.S. Pat. No. 5,240,681 shows a foot exerciser comprising a cradle for engaging the lower leg between the ankle and the knee and a pedal for engaging the foot. The pedal is swingably connected to the cradle with a tension arrangement to provide for swinging resistance. The device includes a stop (80) shown in FIG. 2.

U.S. Pat. No. 5,242,378 discloses an orthopedic brace for supporting the leg of a person. Comprising calf member connected to a thigh member by a knee joint and to a foot member by an ankle joint. Linkage located between the calf member and ankle joint is adjustable during installation on the leg of a person to match the distance between the knee joint and ankle joint with the distance between the knee and ankle of the person. A number of stops are depicted in FIGS. 8 through 10.

U.S. Pat. No. 5,776,090 shows a device for treating Plantar Fasciitis by placing a splint on the dorsal aspect of a wearer's foot, ankle, and fore leg and holding the wearer's foot, toes and ankle in the dorsi flexed position. Reinforcing ribs (28) are depicted in FIG. 1.

U.S. Pat. No. 5,941,913 relates to a single-piece fibre-reinforced plastics shin component for a lower limb prosthesis for an above-knee amputee comprising an energy storing blade and a shin cradle in the form of a channel section including a pair of pivot supports formed as flanges extending away from one of the major surfaces of the blade. Each flange has a pair of holes defining transverse pivot axes, one of which is a knee axis and the other of which is a pivot axis for mounting the distal end of a knee movement control unit. These holes together define a longitudinal axis which is generally parallel to and to the anterior of the blade. The blade merges smoothly into the channel section and, over a distal end portion, is straight and of constant cross-section to allow the blade to be cut to length to suit the amputee.

U.S. Pat. No. 6,689,081 teaches a therapeutic ankle and foot orthosis or brace comprising a lower shell and an upper lateral shell movably coupled together by a pivot so that the shells accommodate the contour, size and shape of the user's foot and ankle. Cushions are included on the shells to provide comfort and straps with hook and pile fasteners are employed to detachably retain the combined shells on the ankle and foot of the user.

U.S. Pat. No. D550,370 shows an articulating ankle brace shell, shown and described.

The following patent documents are additional examples of the prior art: U.S. Pat. No. 1,205,206; U.S. Pat. No. 2,516,872; U.S. Pat. No. 3,528,412; U.S. Pat. No. 4,771,768; U.S. Pat. No. 4,962,760; U.S. Pat. No. 5,056,509; U.S. Pat. No. 5,219,324; U.S. Pat. No. 5,609,568; U.S. Pat. No. 6,019,741; U.S. Pat. No. 7,128,725; U.S. Pat. No. 7,468,004; US 2006/0270958; US 2008/0319361; US 2012/0330206; U.S. Pat. No. D 499,185 and U.S. Pat. No. D 543,281

While some of the prior art may contain some similarities relating to the present invention, none of them teach, suggest or include all of the advantages and unique features of the invention disclosed hereafter.

SUMMARY OF THE INVENTION

The present invention relates to a single piece ankle-foot orthosis constructed of a composite material comprising an upper leg support member coupled to a lower foot support member by an intermediate interconnecting member.

The upper leg support member comprises an arcuate convex shell to engage and support the anterior of the lower leg.

The intermediate interconnecting member comprises an interconnecting member and a lower arcuate convex member having a lateral support extending from each side to the corresponding side of the foot support member to cooperatively form an inverted wishbone or Y configuration integrally coupling the upper leg support member and the lower foot support member.

In an alternate embodiment, the intermediate interconnecting member comprises an upper portion including an interconnecting member and an arcuate convex member terminating in an upper side element or member extending downward from each side thereof and a lower portion including a pair of lateral supports extending from each side of the arcuate convex member of the upper portion to the corresponding side of the foot support member to cooperatively form an inverted wishbone or Y configuration coupling the upper support member and the lower foot support member.

The upper portion of the intermediate interconnecting member is rotatably or pivotally coupled to the lower portion of the intermediate interconnecting member by a coupling assembly disposed on each side of the ankle-foot orthosis.

A limit or stop extends upwardly from the lower portion of the intermediate connecting member to selectively engage the upper leg support member to limit the forward movement of the upper leg support member relative to the lower foot support member when the ankle-foot orthosis is in use.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DESCRIPTION OF THE INVENTION

Figure 1:
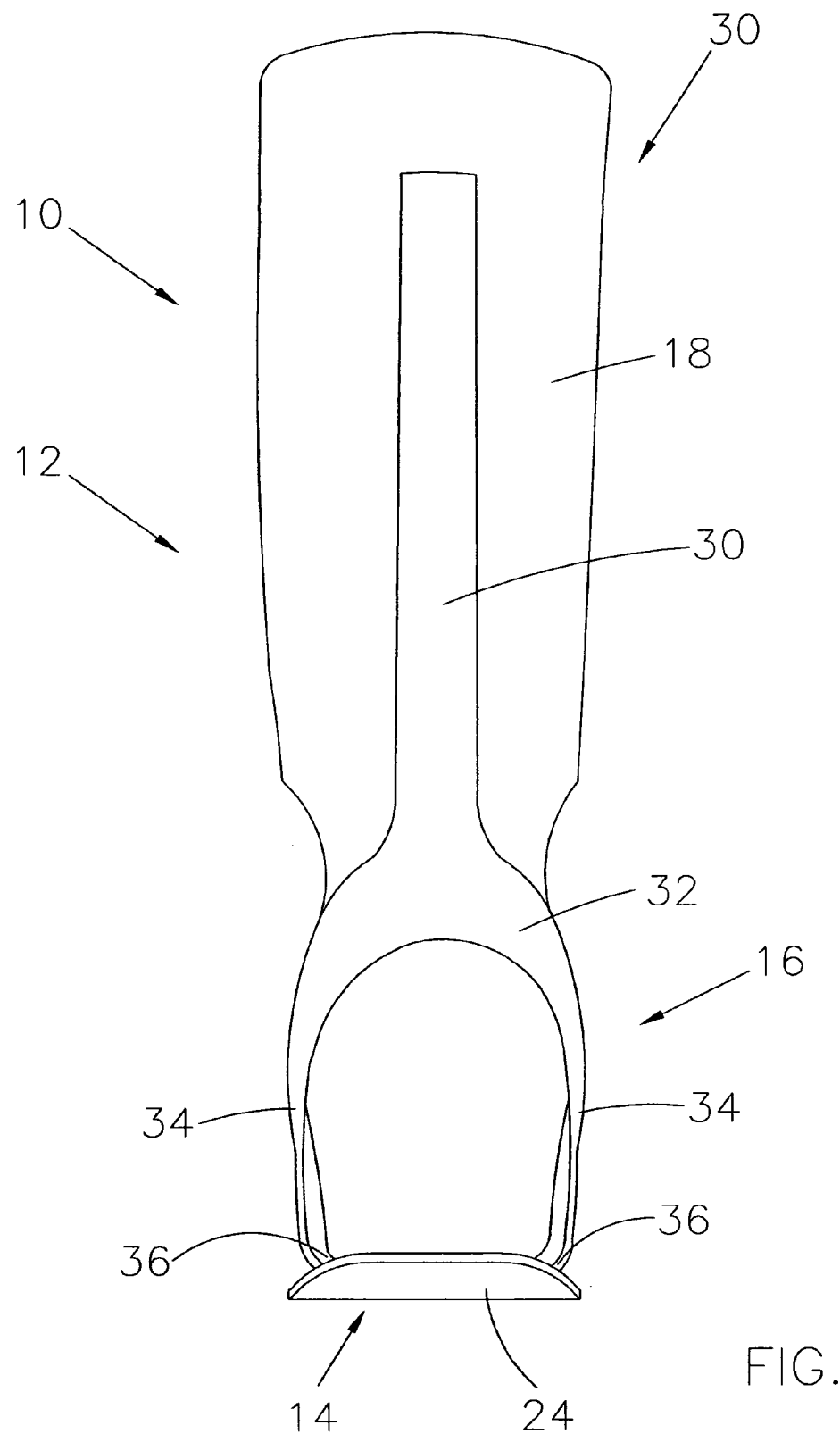
FIG. 1 is a front view of the foot orthosis of the present invention.
Figure 2:
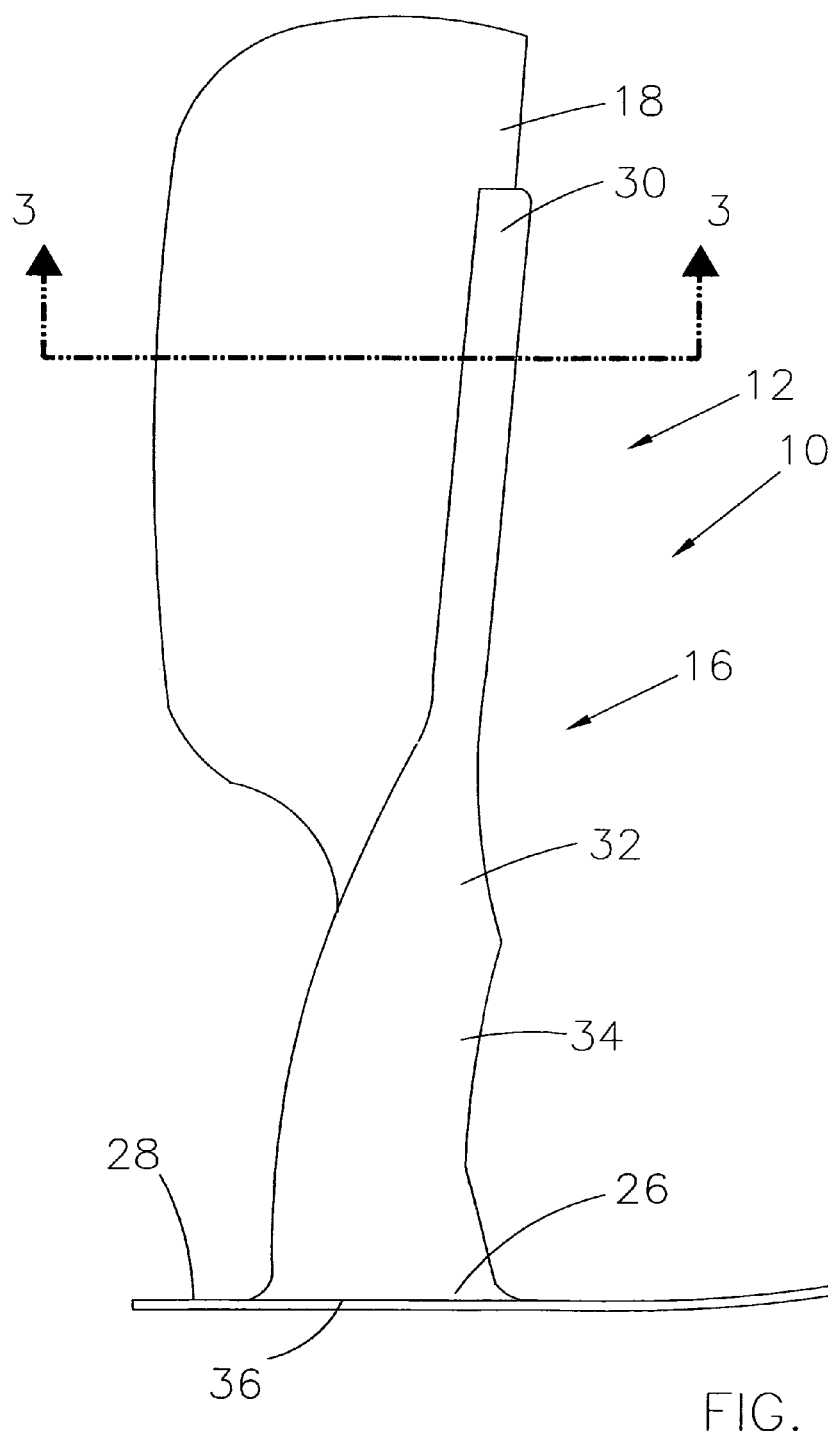
FIG. 2 is a side view of the foot orthosis of the present invention.
Figure 3:
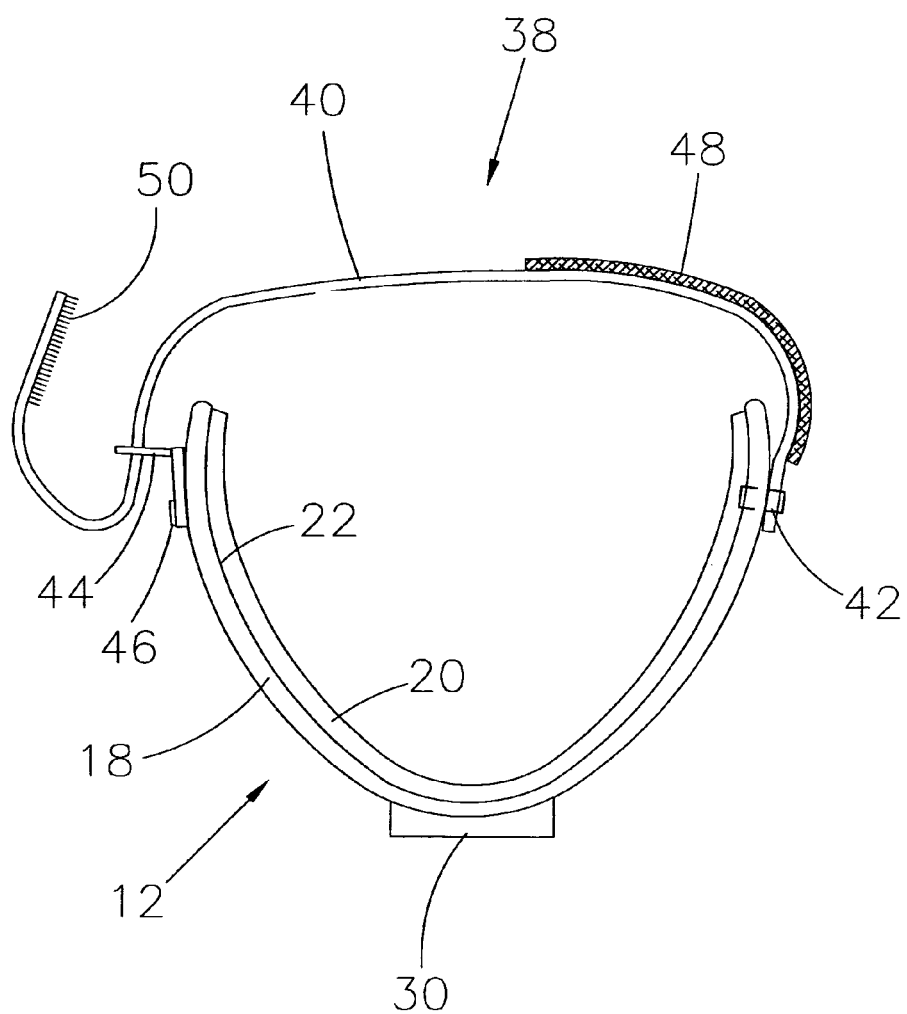
FIG. 3 is a cross-sectional view of the foot othosis of the present invention taken along line 3-3 of FIG. 2.
Figure 4:
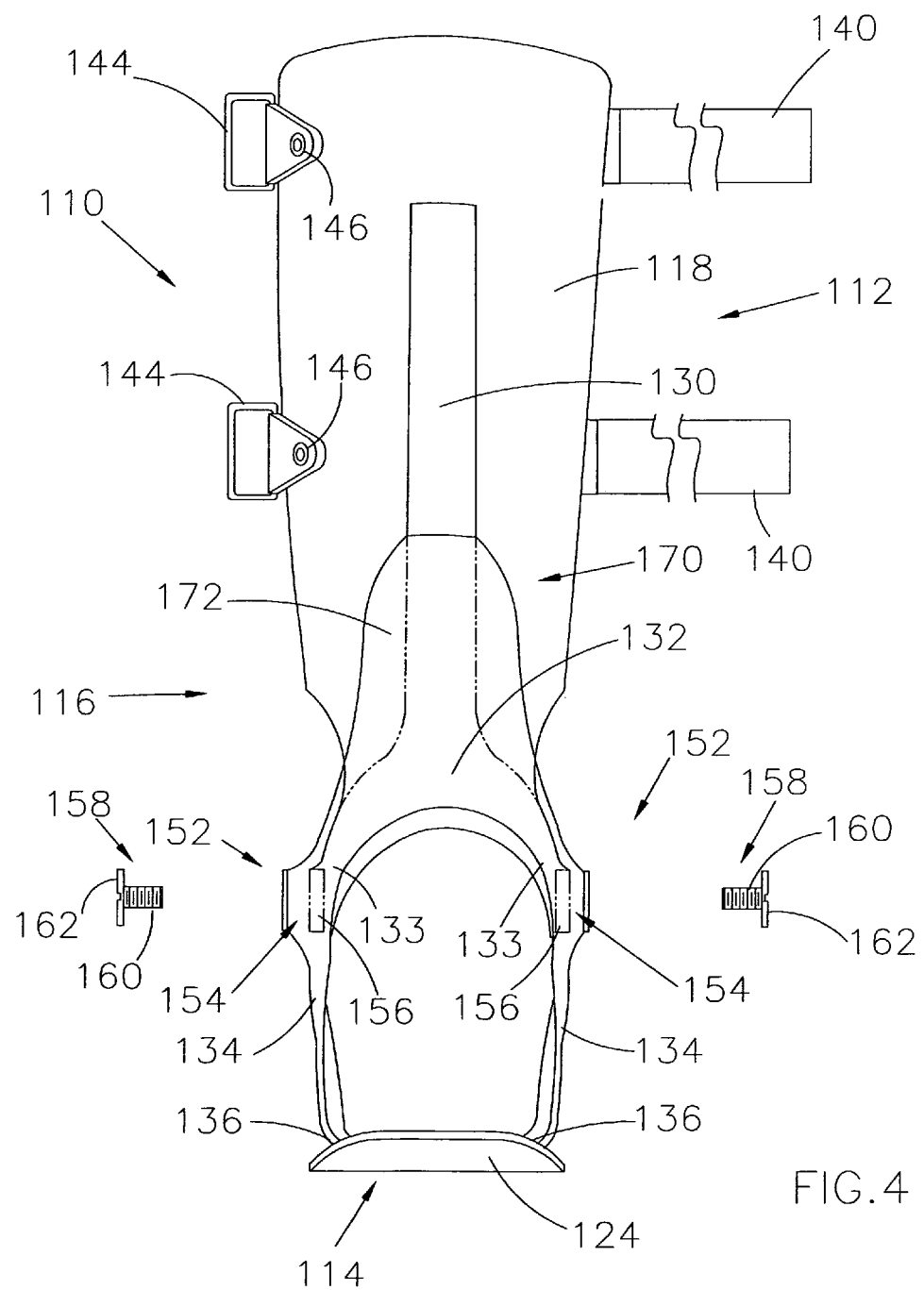
FIG. 4 is a front view of an alternate embodiment of the foot orthosis of the present invention.
Figure 5:
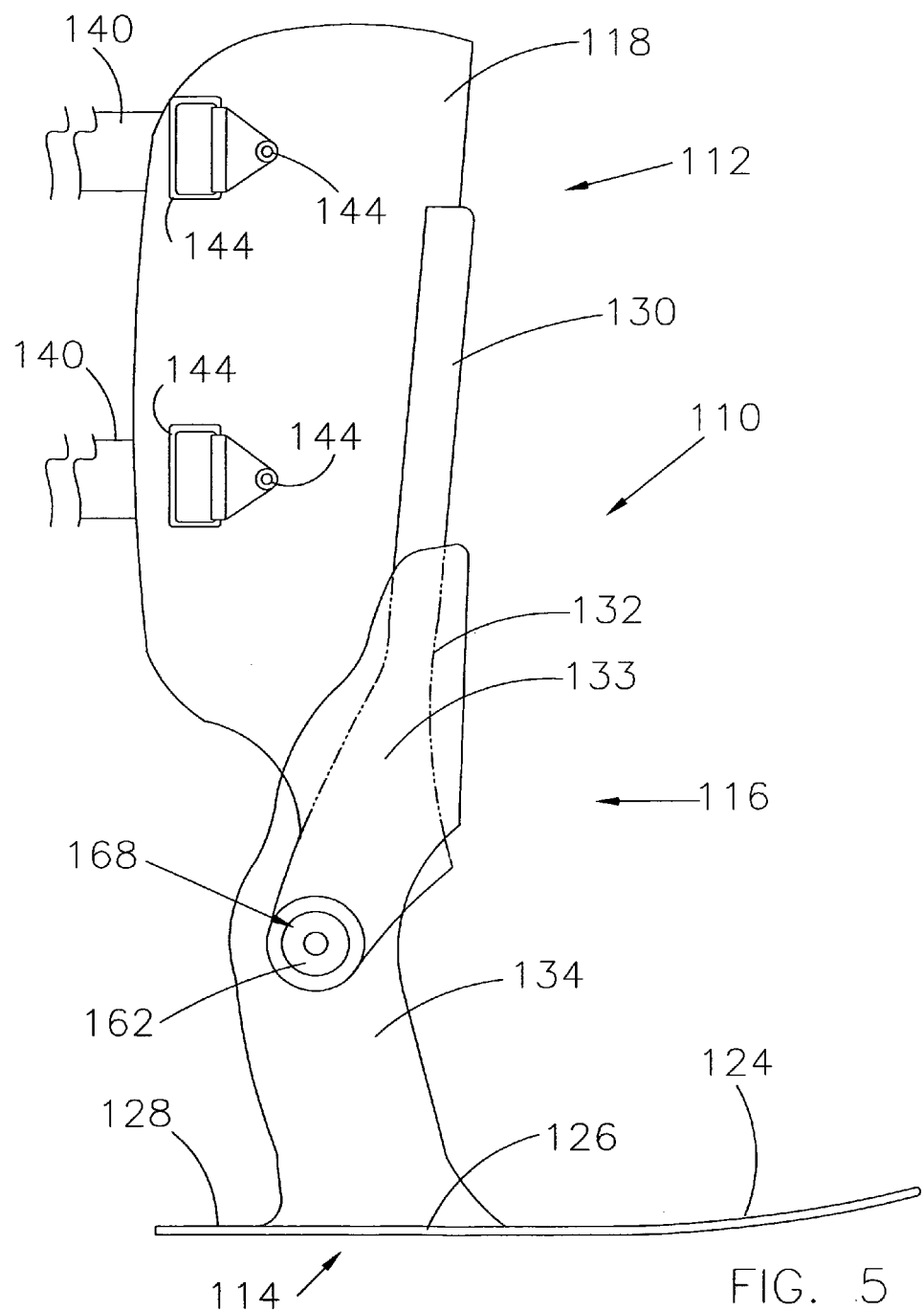
FIG. 5 is a side view of the foot orthosis of the present invention shown in FIG. 4.
Figure 6:
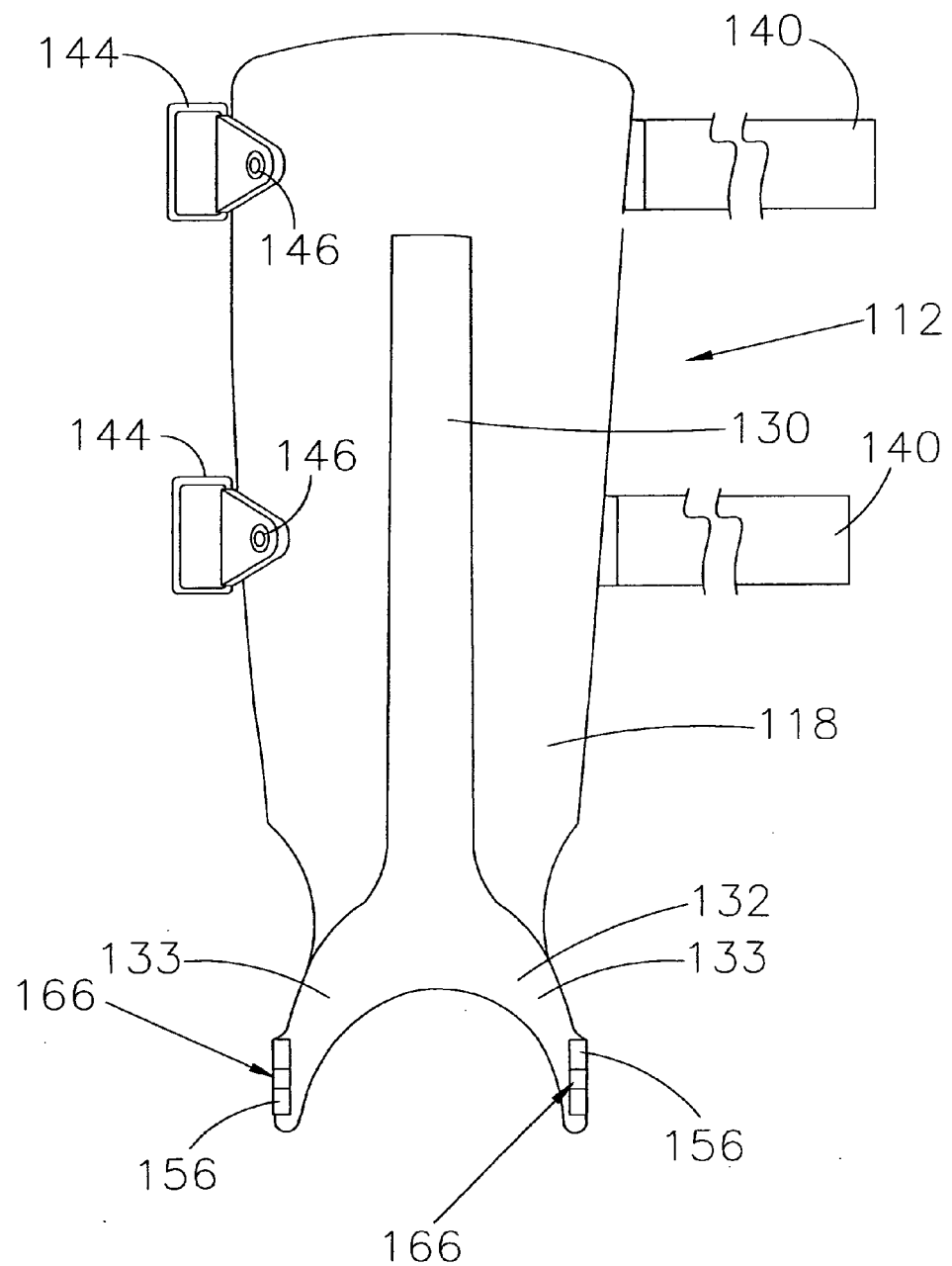
FIG. 6 is a front view of the upper leg support of the foot orthosis of the present invention shown in FIG. 4.
Figure 7:
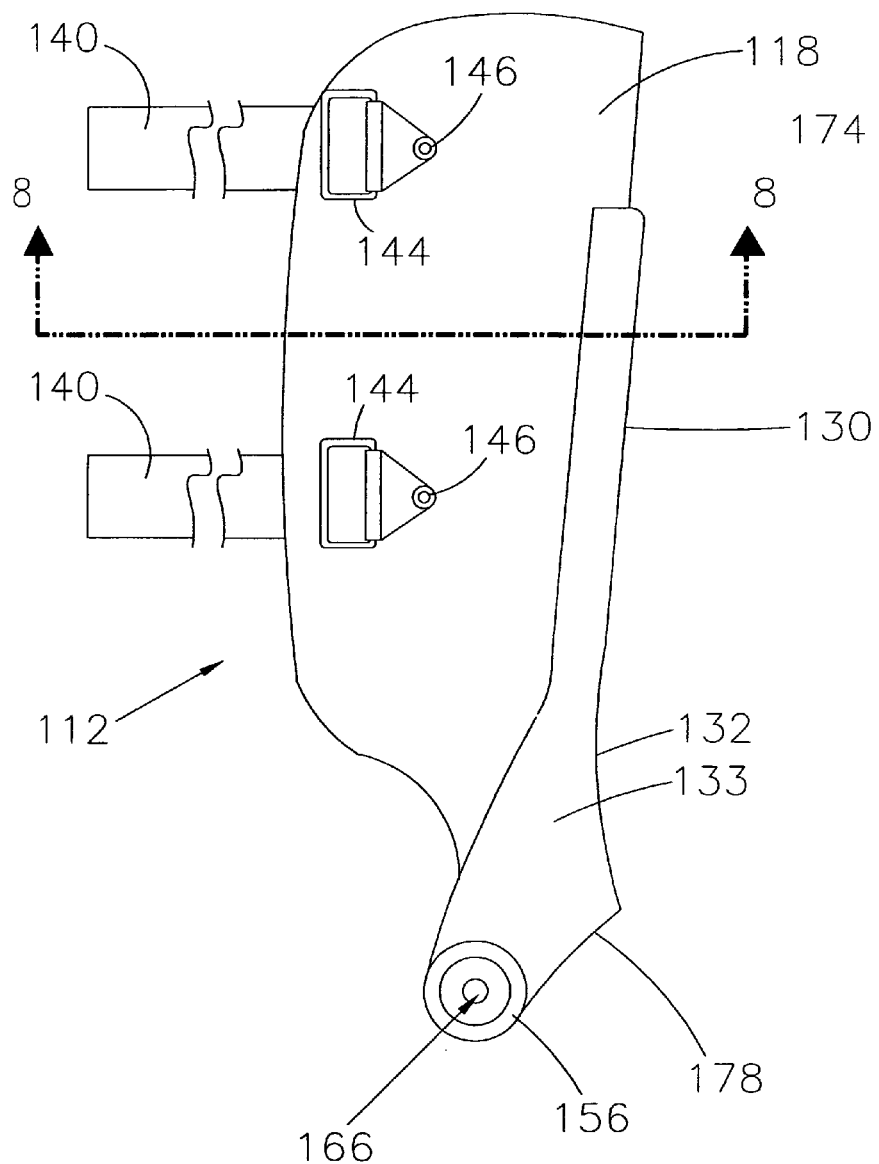
FIG. 7 is a side view of the upper leg support of the upper leg support of the foot orthosis of the present invention shown in FIG. 4.

As shown in FIGS. 1 through 3, the present invention relates to a single piece ankle-foot orthosis generally indicated as 10 constructed of a composite material comprising an upper leg support member generally indicated as 12 coupled to a lower foot support member generally indicated as 14 by an intermediate interconnecting member generally indicated as 16.

The upper leg support member 12 comprises an arcuate convex shell 18 having a pad liner 20 on the inner surface 22 thereof to engage and support the anterior of the lower leg.

The lower foot support member 14 comprising an upwardly arching front toe portion 24, a mid-arch portion 26 and a rear heel portion 28.

The intermediate interconnecting member 16 comprises an upper elongated substantially vertical interconnecting member 30 and a lower arcuate convex member 32 having a lateral support 34 extending from each side thereof to the corresponding side 36 of the foot support member 14 to cooperatively form an inverted wishbone or Y configuration integrally coupling the upper leg support member 12 and the lower foot support member 14.

As shown in FIG. 3, the ankle-foot orthosis includes at least one attachment device generally indicated as 38 to selectively secure the ankle-foot orthosis 10 to the lower leg and foot. The attachment device 38 may comprise a strap 40 affixed to the arcuate convex shell 18 of the upper leg support member 12 by a fastener 42 and a loop 44 affixed to the opposite side of an arcuate convex shell 18 of the upper leg support member 12 by a fastener 46 to receive the strap 40 therethrough. The strap 40 is then secured in place by a buckle or Velcro (loops and hooks) fastener 48 and 50.

FIGS. 4 through 10 show an alternate embodiment of the ankle-foot orthosis of the present invention. Specifically, the ankle-foot orthosis generally indicated as 110 comprising an upper support member generally indicated as 112 coupled to a lower foot support member generally indicated as 114 by an intermediate interconnecting member generally indicated as 116.

The upper leg support member 112 comprises an arcuate convex shell 118 having a pad liner 120 on the inner surface 122 thereof to engage and support the anterior of the lower leg.

The lower support member 114 comprising an upwardly arching front toe portion 124, a mid-arch portion 126 and a rear heel portion 128.

The intermediate interconnecting member 116 comprises an upper portion including an elongated substantially vertical interconnecting member 130 and arcuate convex member 132 terminating in an upper side element or member 133 extending downward from each side thereof and a lower portion including a pair of lateral supports each indicated as 134 extending upwardly from the corresponding sides 136 of the lower foot support member 114 and coupled to the upper portion to cooperatively form an inverted wishbone or Y configuration coupling the upper support member 112 and the lower foot support member 114.

Figure 8:
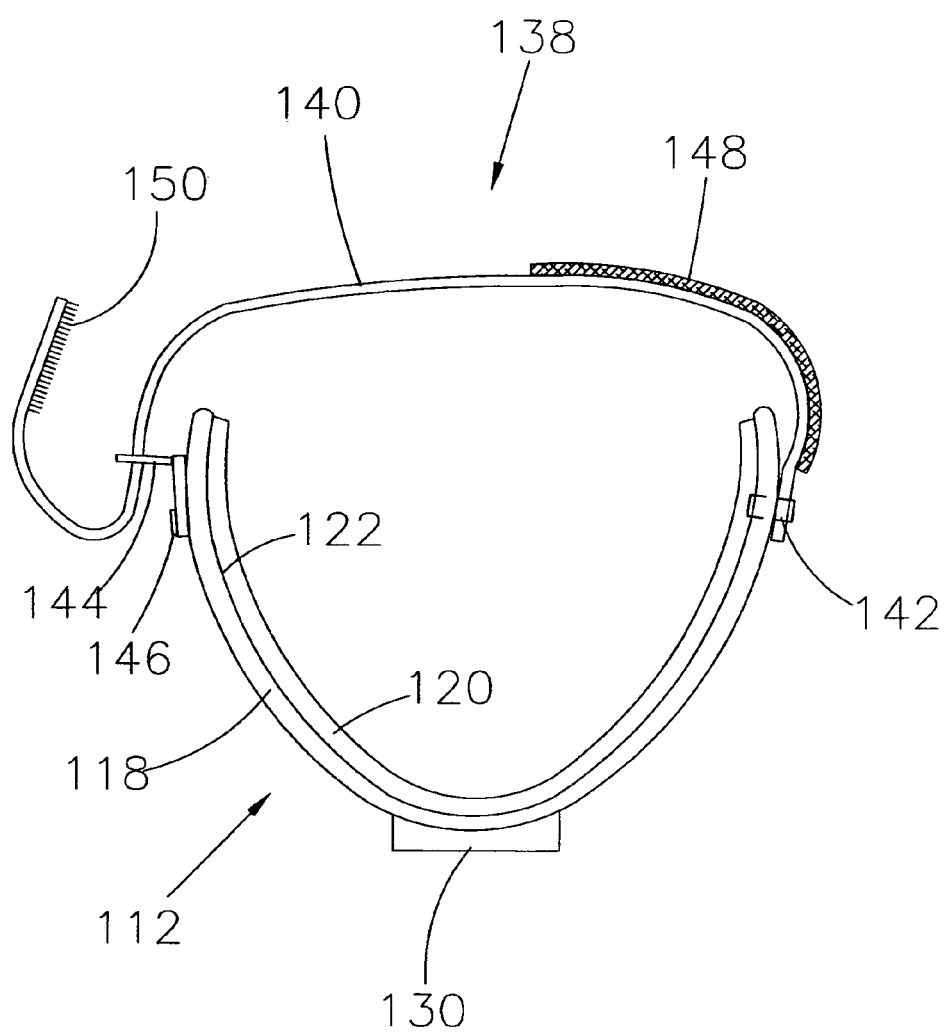
FIG. 8 is a cross-sectional view of the upper leg support of the foot orthosis of the present invention taken along line 8-8 of FIG. 7.
Figure 9:
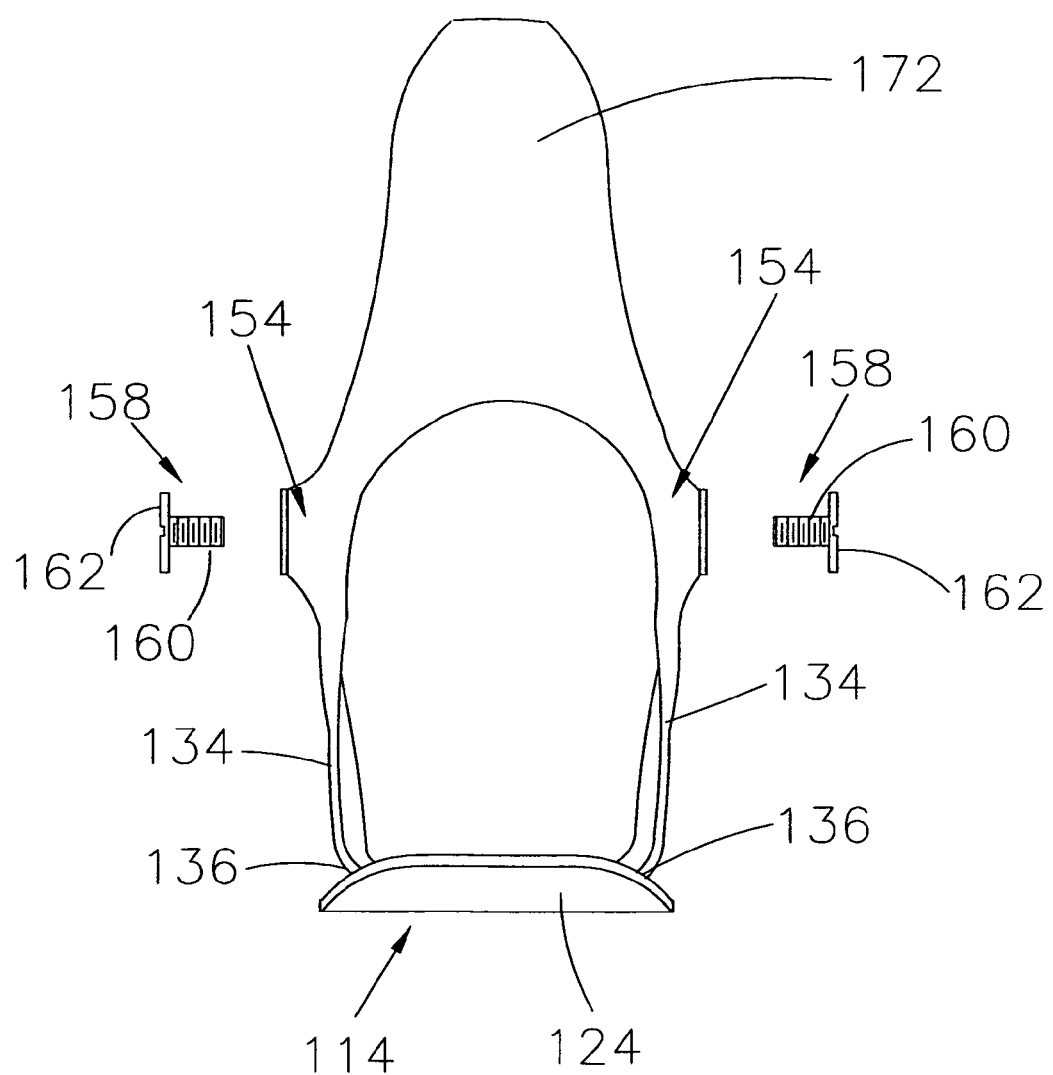
FIG. 9 is a front view of the lower foot support of the foot orthosis of the present shown in FIG. 4.
Figure 10:
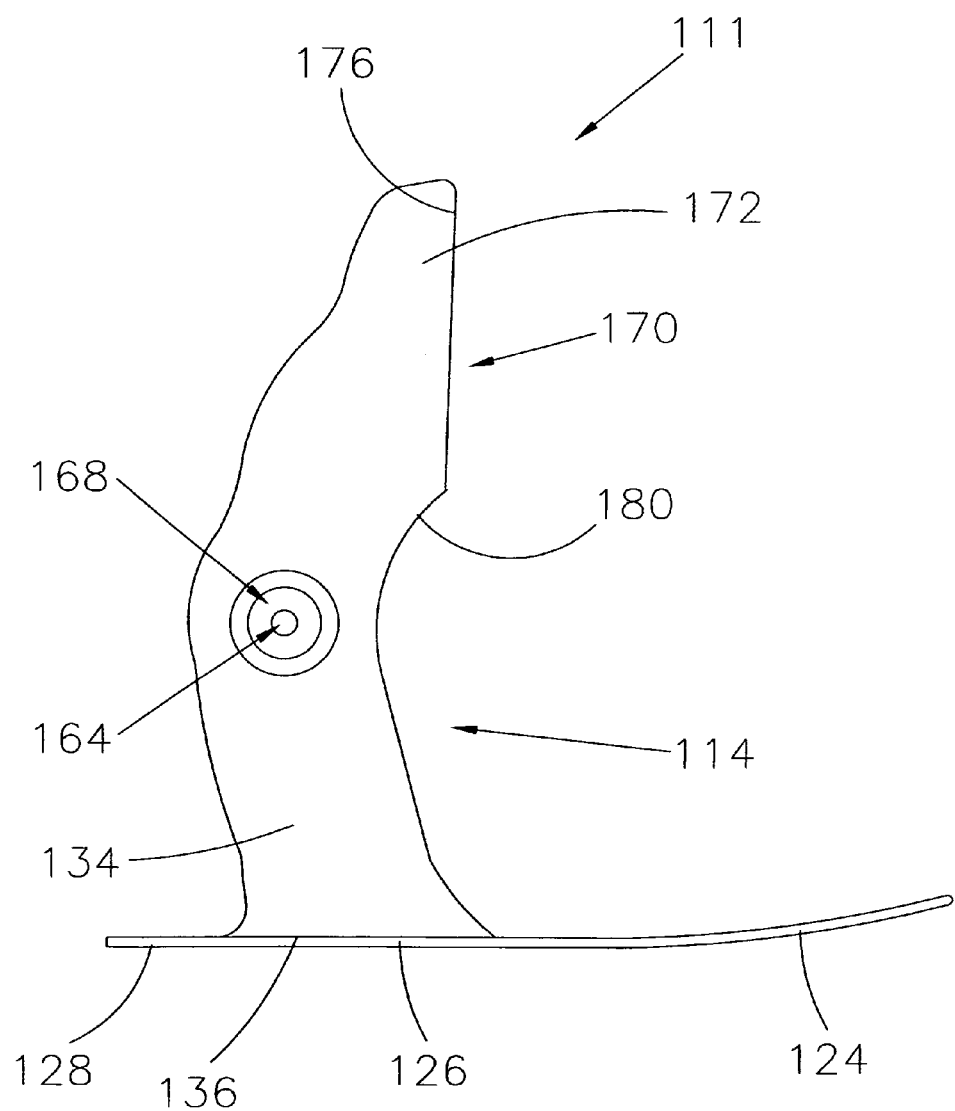
FIG. 10 is a side view of the lower foot support of the foot orthosis of the present invention shown in FIG. 4.

As shown in FIG. 8, the ankle-foot orthosis 110 includes at least one attachment device generally indicated as 138 to selectively secure the ankle-foot orthosis 110 to the lower leg and foot. The attachment device 138 may comprise a strap 140 affixed to the arcuate convex shell 118 of the upper leg support member 112 by a fastener 142 and a loop 144 affixed to the opposite side of an arcuate convex shell 118 of the upper leg support member 112 by a fastener 146 to receive the strap 140 therethrough. The strap 138 is then secured in place by a buckle or Velcro (loops and hooks) fastener 148 and 150.

The upper portion of the intermediate interconnecting member 116 is rotatably or pivotally coupled to the lower portion of the intermediate interconnecting member 116 by a coupling assembly generally indicated as 152 disposed on each side of the ankle-foot orthosis 110. Each coupling assembly 152 comprises a substantially circular coupling recess 154 formed on the upper portion of each lateral support 134 to receive and rotatably support a similarly shaped substantially circular coupling member 156 formed on the lower portion of each downwardly depending upper side element or member 133 to rotatably couple the upper leg support member 112 and the lower foot support member 114 together. A fastener generally indicated as 158 including an elongated externally threaded portion 160 and an enlarged outer portion 162 rotatably fastens the substantially circular coupling member 156 within the corresponding substantially circular coupling recess 154. The elongated externally threaded inner portion 160 is placed through a hole or aperture 164 concentrically aligned with the corresponding substantially circular coupling recess 154 and threaded into an internally threaded hole or recess 166 formed through or in the corresponding substantially circular coupling member 156. Each enlarged outer portion 162 is disposed or seated within a recess 168 formed concentrically with the hole or aperture 164.

A limit or stop generally indicated as 170 extends upwardly from the lower portion of the intermediate member 116 or lateral supports 134 to selectively engage the front or outer surface of the upper leg support member 112 to limit the forward movement of the upper leg support member 112 relative to the lower foot support member 114 when the ankle-foot orthosis 110 is in use.

Specifically, the limit or stop 170 comprises a convex shell 172 having substantially the same curvature as the upper leg support member 112 such that the front or outer surface 174 of the upper leg support member 112 and the inner surface 176 of the convex shell 172 mate or engage to limit the forward rotation of the upper leg support member 112 relative to the lower foot support member 114. The convex limit shell 172 comprises a substantially truncated triangular shape.

The lower edge 178 of the arcuate convex member 132 of the upper portion of the intermediate interconnecting member 116 and the lower edge 180 of the convex limit shell 172 are concave.

Each lateral support 134 is inclined rearwardly and upwardly from the lower foot support member 114 to the corresponding coupling assembly 152.

In use, the single piece ankle-foot orthosis 10 is strapped to the lower leg of the user or patient. As the patient or user walks from heel to toe, the upper leg support member 12 is pivoted or rotated forward until the upper leg support member 12 engages the limit or stop 170 emulating the natural knee action.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described.

What is claimed is:

1. An ankle-foot orthosis constructed of composite material to assist a person with a foot infirmity in walking comprising an upper leg support member including an arcuate convex shell including a lower end portion to engage the anterior of the lower leg and a lower foot support member to engage and support the foot coupled together by an intermediate interconnecting member comprising an upper portion including an upper elongated substantially vertical interconnecting member integrally formed with said upper arcuate convex shell and a lower convex member terminating in an upper side element or member extending downward from each side thereof and a lower portion including a pair of lateral supports extending upwardly from corresponding sides of said lower foot support member and coupled to said upper portion to cooperatively form an Inverted wishbone or Y configuration coupling said upper leg support member and said lower foot support member wherein said upper portion of said intermediate interconnecting member is rotatably or pivotally coupled to said lower portion of said intermediate interconnecting member by a coupling assembly disposed on each side of said ankle-foot orthosis.

2. The ankle-foot orthosis of claim 1 wherein each said coupling assembly comprises a substantially circular coupling recess formed on said upper portion of each said lateral support to receive and rotatably support a similarly shaped substantially circular coupling member formed on said lower portion of each said downwardly depending upper side element or member to rotatably couple said upper leg support member and said lower foot support member together.

3. The ankle-foot orthosis of claim 2 further including a fastener having an elongated externally threaded portion and an enlarged outer portion to rotatably fasten said substantially circular coupling member within said corresponding substantially circular coupling recess.

4. The ankle-foot orthosis of claim 3 wherein each said enlarged outer portion is disposed or seated within a recess formed concentrically with said hole or aperture.

5. The ankle-foot orthosis of claim 3 further including a limit or stop extending upwardly to engage said upper leg support member to limit the forward movement of said upper leg support member relative to said lower foot support member when the ankle-foot orthosis is in use.

6. The ankle-foot orthosis of claim 5 wherein said limit or stop comprises a convex shell having substantially the same curvature as said upper leg support member such that the outer surface of the said upper leg support member and said inner surface of the convex shell engage to limit the forward rotation of said upper leg support member relative to said lower foot support member.

7. The ankle-foot orthosis of claim 6 wherein said convex limit shell comprises a substantially truncated triangular shape.

8. The ankle-foot orthosis of claim 1 wherein said lower edge of the arcuate convex member of the upper portion of the intermediate interconnecting member and the lower edge of the convex limit shell are concave.

9. The ankle-foot orthosis of claim 8 wherein each said lateral support is inclined rearwardly and upwardly from the lower foot support member to the corresponding coupling assembly.

10. The ankle-foot orthosis of claim 1 further including a limit or stop extending upwardly to engage said upper leg support member to limit the forward movement of said upper leg support member relative to said lower foot support member when the ankle-foot orthosis is in use.

11. The ankle-foot orthosis of claim 10 wherein said limit or stop comprises a convex shell having substantially the same curvature as said upper leg support member such that the outer surface of the said upper leg support member and said inner surface of the convex shell engage to limit the forward rotation of said upper leg support member relative to said lower foot support member.

12. The ankle-foot orthosis of claim 11 wherein said convex limit shell comprises a substantially truncated triangular shape.

13. The ankle-foot orthosis of claim 12 wherein said lower edge of the arcuate convex member of the upper portion of the Intermediate interconnecting member and the lower edge of the convex limit shell are concave.

14. The ankle-foot orthosis of claim 13 wherein each said lateral support is inclined rearwardly and upwardly from the lower foot support member to the corresponding coupling assembly.

15. The ankle-foot orthosis of claim 14 wherein at least one attachment device selectively secures said ankle-foot orthosis to the lower leg.

16. The ankle-foot orthosis of claim 15 wherein said attachment device comprises a strap affixed to said arcuate convex shell of the upper leg support member by a fastener and a loop affixed to the opposite side of said arcuate convex shell of said upper leg support member by a fastener to receive said strap therethrough.

17. The ankle-foot orthosis of claim 1 wherein at least one attachment device selectively secures said ankle-foot orthosis to the lower leg.

18. The ankle-foot orthosis of claim 17 wherein said attachment device comprises a strap affixed to said arcuate convex shell of the upper leg support member by a fastener and a loop affixed to the opposite side of said arcuate convex shell of said upper leg support member by a fastener to receive said strap therethrough.

\* \* \* \* \*